(12) United States Patent
Koppe et al.

(10) Patent No.: US 6,813,334 B2
(45) Date of Patent: Nov. 2, 2004

(54) TOMOSYNTHESIS IN A LIMITED ANGULAR RANGE

(75) Inventors: Reiner Koppe, Hamburg (DE); Erhard Paul Arthur Klotz, Neumuenster (DE); Johannes Catharina Antonius Op De Beek, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 176 days.

(21) Appl. No.: 10/082,865

(22) Filed: Oct. 19, 2001

(65) Prior Publication Data

US 2002/0141532 A1 Oct. 3, 2002

(30) Foreign Application Priority Data

Oct. 20, 2000  (EP) ............................................. 00203657

(51) Int. Cl.[7] ............................................. G01N 23/00
(52) U.S. Cl. ........................................................ 378/21
(58) Field of Search .............................. 378/21, 23, 24, 378/27, 62, 4, 5, 6

(56) References Cited

U.S. PATENT DOCUMENTS

| 4,455,668 A | | 6/1984 | Warden ........................ 378/21 |
| 4,516,261 A | * | 5/1985 | Harding et al. .............. 382/131 |
| 5,852,646 A | * | 12/1998 | Klotz et al. ..................... 378/8 |
| 6,666,579 B2 | * | 12/2003 | Jensen ......................... 378/197 |
| 6,744,848 B2 | * | 6/2004 | Stanton et al. ................ 378/55 |
| 2001/0005410 A1 | * | 6/2001 | Rasche et al. .............. 378/197 |
| 2002/0085681 A1 | * | 7/2002 | Jensen ......................... 378/197 |

FOREIGN PATENT DOCUMENTS

| WO | WO0024314 | 4/2000 | ............ A61B/6/00 |

* cited by examiner

Primary Examiner—Eric S. McCall
(74) Attorney, Agent, or Firm—John Vodopia

(57) ABSTRACT

A method and system of forming an X-ray layer image of an object being examined by an X-ray device having an X-ray source and an X-ray detector is described. At least one of the X-ray source and the X-ray detector can be displaced in an angular range around the object in order that X-ray projection images are acquired from different directions. When forming only a single X-ray layer image, or a plurality of X-ray layer images of parallel layers of the object, the time required for the acquisition of the X-ray projection images is notably reduced by forming the X-ray layer image directly from the X-ray projection images, where the resulting X-ray layer image is situated in a plane which extends essentially perpendicularly to the bisector of the angular range of displacement. The angular range of displacement can be less then 180°. The system and method is notably applicable to a C-arm X-ray device, in which the angular range can be chosen at will.

16 Claims, 3 Drawing Sheets

TOMOSYNTHESIS IN A LIMITED ANGULAR RANGE

RELATED APPLICATIONS

This application claims priority under 35 U.S.C. §119 from E.P.O. Patent Application No. 00203657.2 which was filed on Oct. 20, 2000 and is hereby incorporated in its entirety.

BACKGROUND OF THE INVENTION

1. Field of the Invention

The invention relates to a method of forming an X-ray layer image of an object, and to an X-ray device for carrying out such a method.

2. Description of the Related Art

The formation of X-ray layer images of an object by utilizing tomosynthesis has been known for a long time. In tomosynthesis, the X-ray source and the X-ray detector are displaced in opposite directions in planes extending parallel to the object being examined and parallel to one another; and then X-ray projection images of the object being examined are acquired from different positions. Using suitable reconstruction methods, layer images of layers of the object being examined can be formed from such X-ray projection images, where said layer images extend parallel to the planes in which the X-ray source and the X-ray detector were moved.

It is also known to move the X-ray source and the X-ray detector along circular trajectories around the object being examined, for example, by means of a C-arm. In the prior art, it has been assumed that a complete data set is necessary for the reconstruction of high quality layer images; for this purpose the X-ray source and the X-ray detector must be displaced through an angular range of at least 180° around the object being examined. This 180° displacement was also necessary because layer images were to be formed not only in a single plane or in parallel planes through the object being examined, but also in a plurality of preferably mutually perpendicular planes through the object being examined.

SUMMARY OF THE INVENTION

It is an object of the present invention to provide a method of and a device for forming an X-ray layer image of adequate image quality in a single plane or in mutually parallel planes while using less images, less angular range, or a shorter period of time.

The invention is based on the idea that the formation of a layer image in a single plane or in parallel planes does not necessitate displacement of the X-ray source and the X-ray detector through at least 180° around the object being examined; in other words, that acquisition of X-ray projection images from an angular range of less than 180° suffices to form an X-ray layer image of adequate image quality. It has been found that artefacts occur only to a limited extent in an angular range of less than 180°; such artefacts can be ignored for clinical applications. This is particularly true for an X-ray layer image that lies in a plane perpendicular to the bisector of the angular range in which the X-ray source and the X-ray detector are displaced. When use is made of a C-arm X-ray device, as in a preferred embodiment, the bisector thus corresponds to the central pivot position of the X-ray source when it is pivoted from side to side. In other words, the bisector is the center line of the overall angle covering the angular range.

Moreover, the X-ray layer images in accordance with the invention are calculated directly from the X-ray projection images, as opposed to prior art methods where they are calculated from a 3D data set determined from the X-ray projection images.

Thus, in accordance with the invention, X-ray layer images can be formed in parallel layers in a simple and fast manner, because the angular displacement range to be covered is smaller than in the prior art methods. On the other hand, the speed of rotation of the X-ray source and the X-ray detector may also be reduced and the period of time during which a contrast agent is present in the object being examined can be used more effectively.

In a further version of the invention, the position of the angular range relative to the object being examined can be changed so as to image differently oriented layers.

In preferred embodiments of the method in accordance with the invention, the total angular range is from 90° to 180° or, depending on the relevant application, to even less than 90°. It has been found that an image quality which is sufficient for various clinical applications as well as for adequate suppression of artefacts can also be achieved using an angular range of less than 150°. However, when the angular range is reduced further, contour lines of object details in the examination zone are become more and more blurred.

In order to further reduce the time required for the acquisition of the X-ray projection images and the formation of the X-ray layer image, the number of X-ray projection images to be acquired for the formation of the X-ray layer image can be limited in further preferred embodiments of the invention. Granted, the image quality generally is higher when the number of projection images is larger, because the reconstruction artefacts are more spread. However, it has been found that adequate image quality can be achieved by using a number of no more than 100 X-ray projection images; and, for specific applications, a maximum number of 80 X-ray projection images is sufficient. The reduction of the number of images also leads to a reduction of the radiation dose.

Furthermore, in a preferred embodiment, a plurality of essentially parallel X-ray layer images of the object being examined are formed from the acquired X-ray projection images. This is possible because, in accordance with the invention, the image quality suffices for essentially parallel X-ray layer images, in contrast to the image quality of X-ray layer images of layers that are situated essentially parallel to the bisector would be significantly poorer and inadequate for clinical applications.

In accordance with the invention, a C-arm X-ray device is advantageously used for the acquisition of the x-ray projection images.

It may also be advantageous to combine a plurality of X-ray layer images of neighboring thin layers so as to form an X-ray layer image of a thicker layer.

For the acquisition of the X-ray projection images, the X-ray source and the X-ray detector can be displaced either along a circular trajectory or in opposite parallel planes around the object being examined as in the case of the known tomosynthesis. Furthermore, it may also be arranged that only the X-ray source or only the X-ray detector is displaced in a single plane around the object being examined while the other element is stationary.

BRIEF DESCRIPTION OF THE DRAWINGS

The invention will be described in detail hereinafter with reference to the drawing. Therein.

DETAILED DESCRIPTION OF THE PRESENTLY PREFERRED EMBODIMENT

Figure 1:
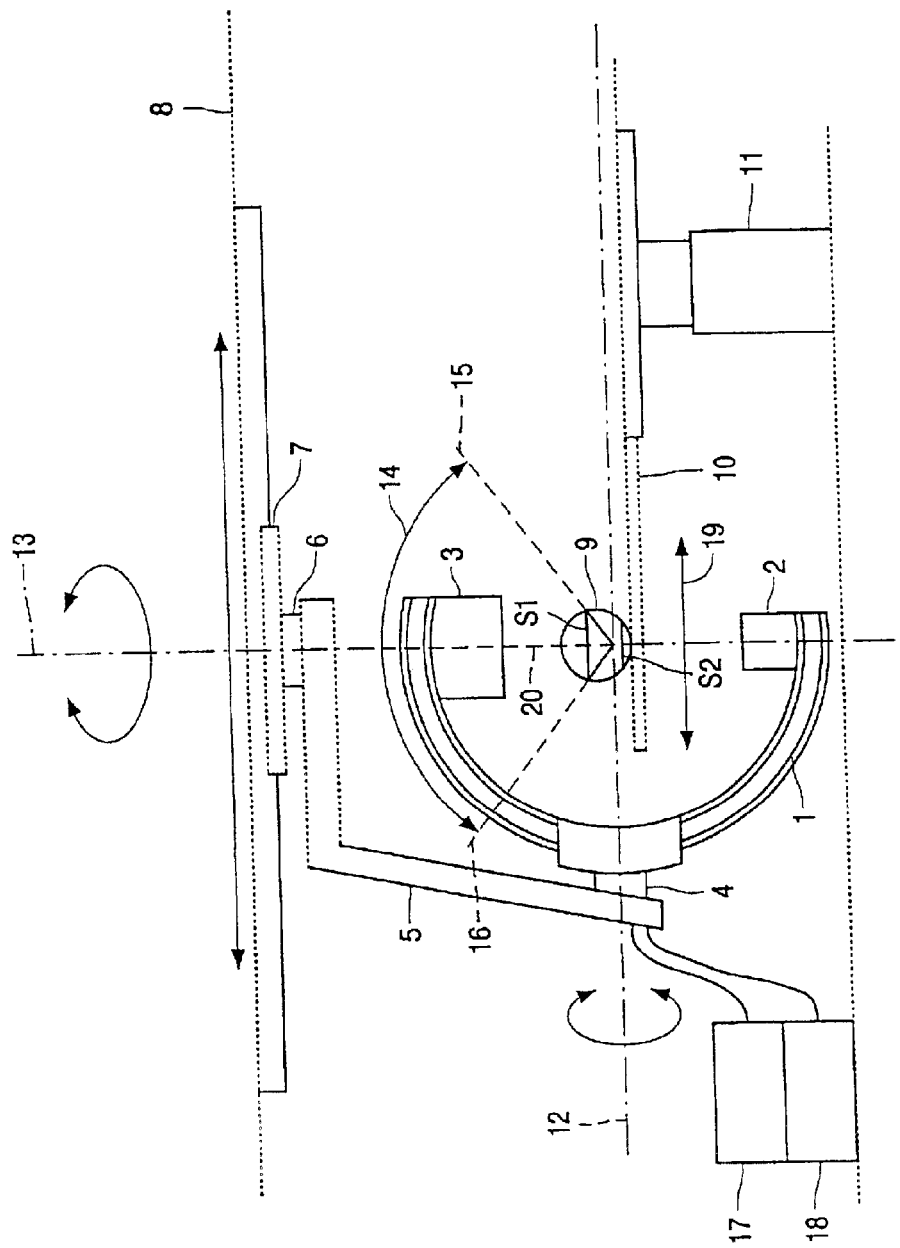
FIG. 1 shows a C-arm X-ray device in accordance with the invention.

An X-ray device in accordance with the invention as shown in FIG. 1 includes a C-arm 1, the ends of which accommodate an X-ray source 2 and a facing X-ray detector 3. The C-arm 1 is suspended from an L-arm 5, by way of a pivot 4, so as to be rotatable about the horizontal propeller axis 12. The L-arm 5 is suspended from a displaceable carriage 7 by way of a further pivot 6; said carriage is suspended from the ceiling 8. The pivot 6 enables rotation about the vertical axis 13. The L-arm 5 can be displaced in the horizontal direction by way of the carriage 7. An object 9 being examined (symbolically shown), for example a patient, is arranged on a patient table 10; and said patient table is mounted on a base 11 whose height can be adjusted and which is also displaceable in the horizontal direction 19. A control unit 17 controls the X-ray device. Image processing, in particular, the formation of X-ray layer images from the acquired X-ray projection images, is performed by means of an image processing unit 18.

For various clinical applications, it is often necessary to form only a single X-ray layer image of a single layer S1 or a plurality of layer images of parallel layers S1, S2 of the object 9 being examined. According to prior art methods, a complete three-dimensional data set of the region of interest (ROI) of the object being examined is first acquired in order to calculate and reproduce one or more X-ray layer images therefrom by means of a suitable reconstruction method. For the acquisition of a complete three-dimensional data set, however, it is necessary to acquire X-ray projection images from a minimum range so as to satisfy the so-called condition of completeness. To this end, it is necessary at least to acquire X-ray projection images using an angular range of at least 180°, which means that the X-ray source 2 and the X-ray detector 3 are rotated along a trajectory in the form of a half circle around the object 9 being examined, for example, around the propeller axis 12 or around an axis that extends perpendicularly to the plane of drawing and through the point of intersection of the axes 12 and 13. X-ray projection images are then acquired from different angular positions in order to extract the data for the three-dimensional data set therefrom. In order to obtain more data, all trajectories in the form of two mutually perpendicular half circles or in the form of one or two mutually perpendicular full circles are taken.

Such prior art methods have the drawback that the acquisition of the three-dimensional data set and the formation of one or more X-ray layer images therefrom require a comparatively long period of time. Moreover, it is often impossible to acquire all X-ray projection images during a single rotary motion of the C-arm 1; for example, in the case of trajectories in the form of two mutually perpendicular half circles, it is necessary to interrupt the acquisition of the X-ray projection images after completion of the first half circle trajectory, to move the C-arm to the starting position of the second half circle trajectory, and to subsequently acquire the remaining X-ray projection images. This takes up an additional period of time and it is often not possible to execute this operation with only a single injection of the contrast agent which is required for certain clinical applications.

However, the expenditure for the acquisition of the X-ray projection images can be significantly reduced, in accordance with the present invention, when it is only necessary to form a single X-ray layer image or a plurality of X-ray layer images of parallel layers. This is because in this case it is sufficient to acquire X-ray projection images from only a limited angular range, that is, an angular range less than 180°, and to determine the X-ray layer images therefrom. For example, when X-ray layer images of the layers S1 and S2 of the object 9 being examined have to be formed, it suffices to acquire X-ray projection images exclusively from the angular range 14, which means that the C-arm 1 only has to be displaced between the starting position 15 and the final position 16; the X-ray projection images are acquired from different directions during such displacement. The angular range 14 is positioned in such a manner that the bisector 20 of this angular range 14 extends essentially perpendicularly to the layers S1 and S2 of interest. when X-ray layer images are to be formed for other layers that are not situated parallel to the layer S1, the angular range 14 is positioned accordingly so that the bisector again extends essentially perpendicularly to these layers. Layer images of layers that do not extend exactly perpendicularly to the bisector 20 can also be formed from the X-ray projection images acquired; however, the image quality then becomes poorer as the deviation relative to the perpendicular position is larger.

In accordance with the invention, the X-ray layer images are calculated from the acquired X-ray projection images by tomosynthesis utilizing a suitable reconstruction method, for example the Feldkamp algorithm or partial backprojection. The X-ray layer images are then formed directly from the X-ray projection images, that is, without the formation of a three-dimensional data set as in the prior art methods. In accordance with the invention, the angular range 14 amounts to less than 180° and can be reduced even further depending on the relevant application and the desired image quality.

Figure 2:
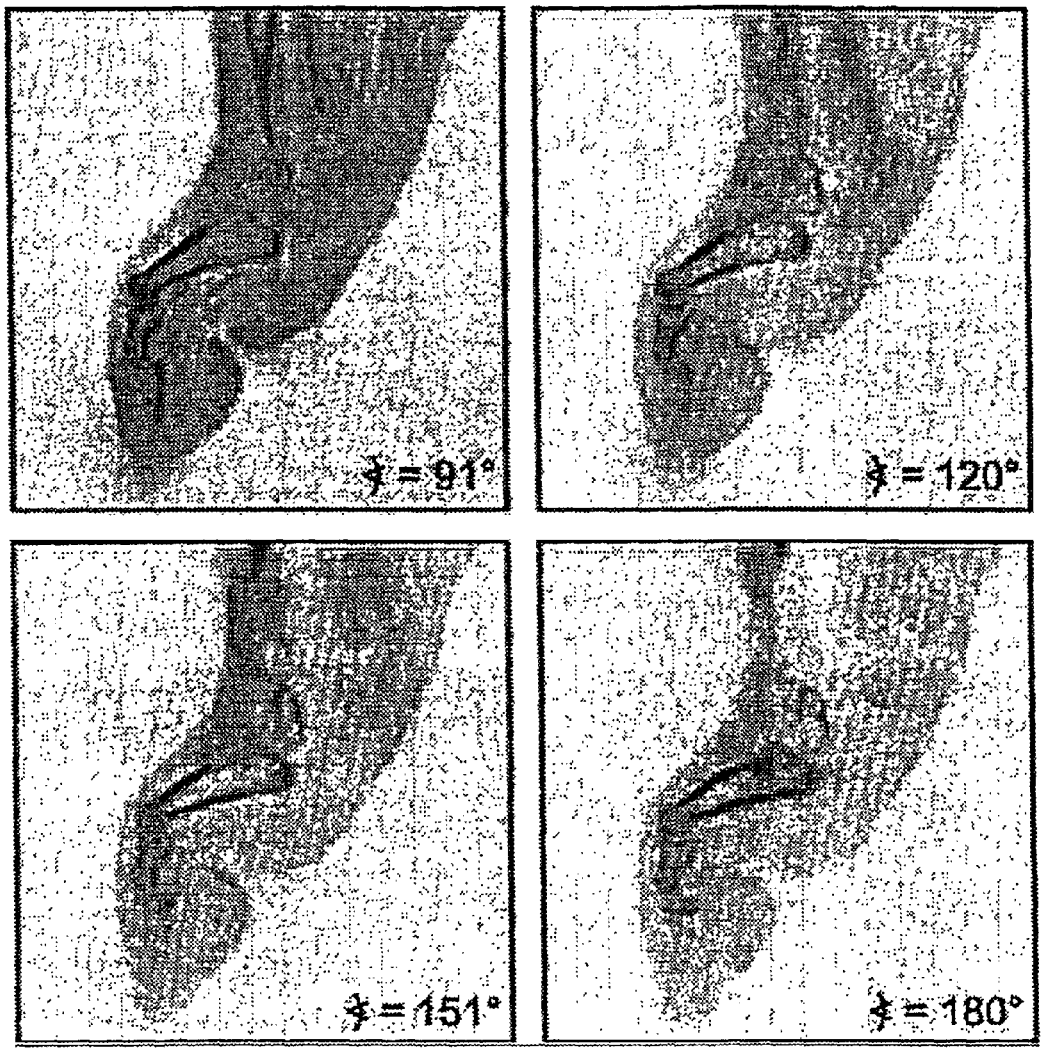
FIG. 2 shows X-ray layer images of the point of the foot of a patient that have been formed by means of X-ray layer images from different angular ranges.

The results of a practical application of the present invention can be seen in FIG. 2, which shows X-ray layer images of the point of the foot of a patient which were formed with reduced angular ranges. The gaps between the toe bones (arrowhead) is clearly visible in the lower two images; whereas in the upper two images, formed from X-ray projection images using angular ranges of 91° and 120°, respectively, the resolution is more blurred and the boundaries of the elements shown are no longer clearly visible. The artefacts, however, are negligibly small in all four images.

Figure 3:
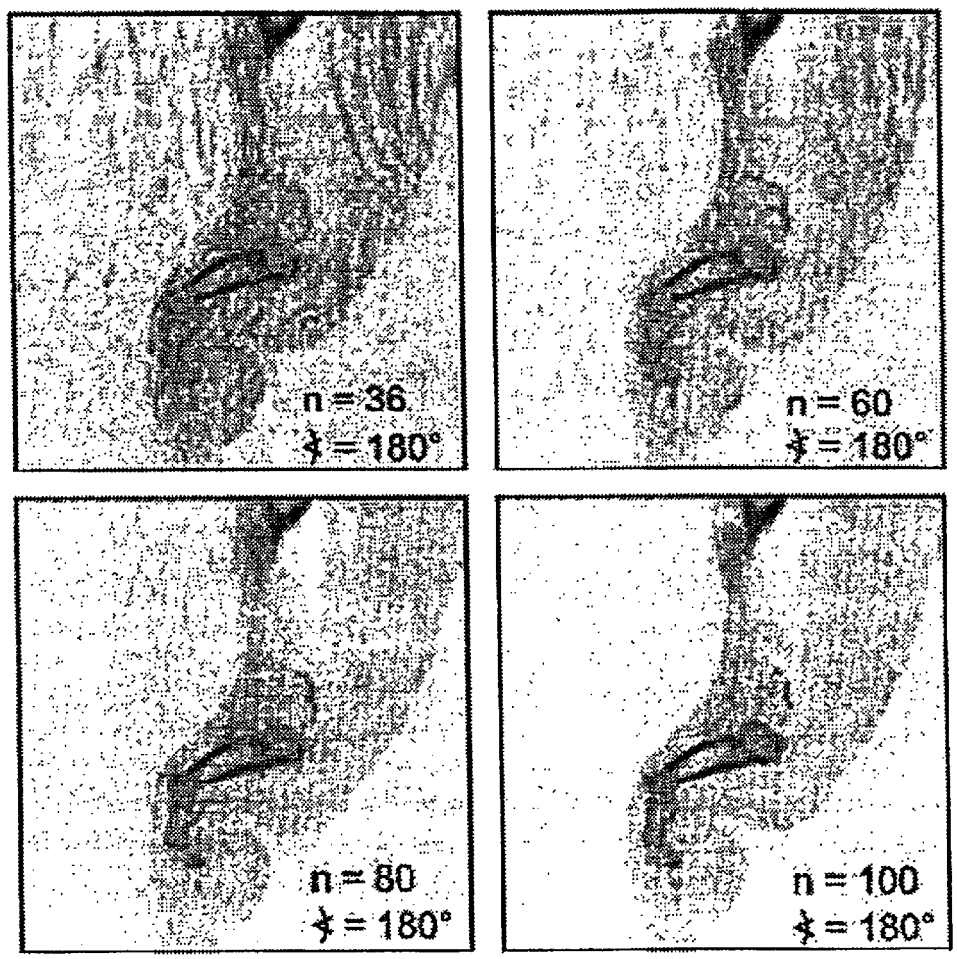
FIG. 3 shows X-ray layer images of the point of the foot that have been formed from different numbers of X-ray projection images.

In accordance with the invention, the number of X-ray projection images for forming an X-ray layer image can be reduced in comparison with the prior art method. For example, in one application X-ray layer images of the point of the foot were acquired with 36, 60, 80 and 100 X-ray projection images from each time an angular range of 180° and respective X-ray layer images were formed therefrom. The results are shown in FIG. 3. The resolution and the effects of artefacts are acceptable in the lower two layer images (n=80; n=100), whereas the artefacts are too pronounced in the upper two images. For clinical applications, however, the X-ray layer image that has been formed from 80 X-ray projection images may suffice. Additionally, the angular range can be suitably chosen as enabled by the C-arm X-ray device shown.

It is to be emphasized again that the invention is not restricted to the embodiment shown. It is possible to arrange the X-ray source and the X-ray detector, instead of on a C-arm, in parallel planes relative to one another while using a suitable mechanical system, the object being examined being situated between said planes. The X-ray ray source and the X-ray detector are preferably moved in opposite directions in such an arrangement, so that the projection lines (i.e., the connecting lines between the X-ray source and the X-ray detector) always intersect in the examination zone. Moreover, it may be arranged that only the X-ray detector or only the X-ray source is moved.

What is claimed is:

1. A method of forming an X-ray layer image of an object with an X-ray device having an X-ray source and an X-ray detector, comprising the steps of:

displacing the X-ray source and the X-ray detector in an angular range around the object in order to acquire X-ray projection images; and forming an X-ray layer image directly from the X-ray projection images without creating an intermediary three-dimensional data set, the formed X-ray layer image being situated in a plane which extends essentially perpendicularly to a bisector of the angular range;

wherein the angular range of displacement is less than 180°.

2. The method as claimed in claim 1, wherein the position of the angular range relative to the object can be changed.

3. The method as claimed in claim 1, wherein the angular range lies between 90° and 180°.

4. The method as claimed in claim 1, wherein the angular range is less than 90°.

5. The method as claimed in claim 1, wherein 100 or less X-ray projection images are acquired in order to form the X-ray layer image.

6. The method as claimed in claim 1, wherein no more than about 80 X-ray projection images are acquired in order to form the X-ray layer image.

7. The method as claimed in claim 1, wherein a plurality of X-ray layer images of the object which extend essentially parallel to one another are formed from the acquired X-ray projection images.

8. The method as claimed in claim 1, wherein the X-ray projection images are acquired by means of a C-arm X-ray device.

9. The method as claimed in claim 1, wherein a plurality of X-ray layer images of neighboring thin layers are combined in order to form an X-ray layer image of a thicker slice.

10. The method as claimed in claim 1, wherein the X-ray source and the X-ray detector are displaced along a circular trajectory around the object in order to acquire X-ray projection images.

11. The method as claimed in claim 1, wherein the X-ray source and the X-ray detector are displaced in opposite directions in parallel planes in order to acquire X-ray projection images.

12. The method as claimed in claim 11, wherein only one of the X-ray source or the X-ray detector is displaced in order to acquire X-ray projection images.

13. An X-ray device comprising:

an X-ray source and an X-ray detector, each situated on an opposite side of an object being examined for the acquisition of X-ray projection images of the object, wherein at least one of the X-ray source and the X-ray detector are movable so that X-ray projection images are acquired in an angular range around the object;

an image processing unit for forming an X-ray layer image from the X-ray projection images; and a control unit for controlling the X-ray device;

wherein only X-ray projection images in an angular range of less than 180° are acquired in order to form the X-ray layer image; and wherein the image processing unit forms the X-ray layer image directly from the X-ray projection images without creating an intermediary three-dimensional data set, where the formed X-ray layer image is situated in a plane which extends essentially perpendicularly to a bisector of the angular range.

14. The X-ray device as claimed in claim 13, wherein the X-ray device includes a C-arm system.

15. The method as claimed in claim 1, wherein between about 60 and about 80 X-ray projection images are acquired in order to form the X-ray layer image.

16. A method of forming an X-ray layer image of an object with an X-ray device having an X-ray source and an X-ray detector, comprising the steps of:

displacing the X-ray source and the X-ray detector over a less than 180° angular range around an object being examined in order to acquire less than 100 X-ray projection images; and forming at least one X-ray layer image directly from the less than 100 X-ray projection images without creating an intermediary three-dimensional data set, the formed X-ray layer image being situated in a plane which extends essentially perpendicularly to a bisector of the angular range.

* * * * *